(12) United States Patent
Kihara

(10) Patent No.: US 10,888,841 B2
(45) Date of Patent: Jan. 12, 2021

(54) AFFINITY CHROMATOGRAPHY CARRIER AND METHOD FOR PURIFYING BIOLOGICAL SUBSTANCE

(71) Applicant: FUJIFILM Corporation, Tokyo (JP)

(72) Inventor: Shiori Kihara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 384 days.

(21) Appl. No.: 15/952,627

(22) Filed: Apr. 13, 2018

(65) Prior Publication Data

US 2018/0229215 A1 Aug. 16, 2018

Related U.S. Application Data

(63) Continuation of application No. PCT/JP2016/081312, filed on Oct. 21, 2016.

(30) Foreign Application Priority Data

Oct. 23, 2015 (JP) ................................. 2015-208982

(51) Int. Cl.

| | |
|---|---|
| *B01J 20/286* | (2006.01) |
| *B01D 15/08* | (2006.01) |
| *B01J 20/28* | (2006.01) |
| *B01J 20/291* | (2006.01) |
| *B01J 20/32* | (2006.01) |
| *B01J 20/285* | (2006.01) |
| *B01D 15/38* | (2006.01) |
| *C07K 16/00* | (2006.01) |
| *C07K 1/22* | (2006.01) |
| *B01J 20/24* | (2006.01) |
| *G01N 30/88* | (2006.01) |

(52) U.S. Cl.
CPC ............ *B01J 20/286* (2013.01); *B01D 15/08* (2013.01); *B01D 15/3809* (2013.01); *B01J 20/24* (2013.01); *B01J 20/28* (2013.01); *B01J 20/285* (2013.01); *B01J 20/291* (2013.01); *B01J 20/3208* (2013.01); *B01J 20/3217* (2013.01); *B01J 20/3274* (2013.01); *B01J 20/3293* (2013.01); *C07K 1/22* (2013.01); *C07K 16/00* (2013.01); *G01N 30/88* (2013.01)

(58) Field of Classification Search
CPC ........ B01J 20/286; B01J 20/28; B01J 20/291; B01J 20/3293; B01J 20/3274; B01J 20/3217; B01J 20/285; B01J 20/3208; B01D 15/08; B01D 15/3809; C07K 16/00; C07K 1/22

See application file for complete search history.

(56) References Cited

U.S. PATENT DOCUMENTS

| | | | |
|---|---|---|---|
| 4,663,163 A | 5/1987 | Hou et al. | |
| 4,879,340 A | 11/1989 | Moriguchi et al. | |
| 2010/0320149 A1 | 12/2010 | Axen et al. | |
| 2011/0301330 A1 | 12/2011 | Matsumoto et al. | |
| 2015/0225445 A1 | 8/2015 | Minakuchi | |
| 2016/0083419 A1 | 3/2016 | Taniguchi et al. | |
| 2016/0237113 A1* | 8/2016 | Minakuchi | ............... C07K 1/22 |

FOREIGN PATENT DOCUMENTS

| | | |
|---|---|---|
| CN | 101765458 A | 6/2010 |
| CN | 102326075 A | 1/2012 |
| JP | 63-48222 A | 2/1988 |
| JP | 2010-133734 A | 6/2010 |
| JP | 2010-534336 A | 11/2010 |
| RU | 2367517 C2 | 9/2009 |
| SU | 1700006 A1 | 12/1991 |
| WO | WO 84/03053 A1 | 8/1984 |
| WO | WO 2006/033634 A1 | 3/2006 |
| WO | WO 2010/095673 A1 | 8/2010 |
| WO | WO 2014/034457 A1 | 3/2014 |
| WO | WO 2014/171437 A1 | 10/2014 |

OTHER PUBLICATIONS

Extended European Search Report issued in corresponding European Application No. 16857567.8 and dated Sep. 14, 2018.
European Office Action dated Dec. 20, 2019, for corresponding European Patent Application No. 16857567.8.
International Preliminary Report on Patentability and Written Opinion of the International Searching Authority (Forms PCT/IB/326, PCT/IB/373 and PCT/ISA/237) for Application No. PCT/JP2016/081312, dated May 3, 2018, with an English translation of the Written Opinion.
International Search Report and English translation (Form PCT/ISA/210) for Application No. PCT/JP2016/081312, dated Jan. 24, 2017.
Russian Office Action and Search Report, dated Dec. 27, 2018, for corresponding Russian Application No. 2018114693, with English translations.
Australian Office Action for corresponding Australian Application No. 2016340518, dated Oct. 3, 2018.

(Continued)

*Primary Examiner* — Daniel E Kolker
*Assistant Examiner* — James L Rogers
(74) *Attorney, Agent, or Firm* — Birch, Stewart, Kolasch & Birch, LLP

(57) ABSTRACT

Provided is an affinity chromatography carrier having an excellent purification purity, including a substrate, a hydrophilic polymer, and an affinity ligand, in which the substrate is constituted of at least one selected from the group consisting of a polysaccharide, an acrylate-based polymer, a methacrylate-based polymer and a styrene-based polymer, the hydrophilic polymer is at least one selected from the group consisting of hydrophilic polysaccharides, the affinity ligand is at least one selected from the group consisting of an antibody-binding protein and an antibody-binding polypeptide, a carboxy group is introduced into the affinity chromatography carrier, and the amount of the carboxy group introduced is 15 mmol/L-gel to 60 mmol/L-gel in terms of ion exchange capacity.

12 Claims, No Drawings

(56) References Cited

OTHER PUBLICATIONS

Japanese Office Action, dated Mar. 19, 2019, for corresponding Japanese Application No. 2017-545816 with an English machine translation.
Machine translation of JP-2010-133734-A, published Jun. 17, 2010.
Singapore Written Opinion and Search Report, dated Mar. 20, 2019, for corresponding Singapore Application No. 11201802997W.
Chinese Office Action for corresponding Chinese Application No. 201680060014.X, dated Feb. 19, 2020, with a partial English translation.
Chinese Office Action and Search Report dated Aug. 5, 2019, for corresponding Chinese Patent Application No. 201680060014.X, with partial English translation.
Korean Office Action dated Aug. 5, 2019. For corresponding Korean Patent Application No. 10-2018-7009519, with English translation.
Canadian Office Action dated May 13, 2019, for corresponding Canadian Patent Application No. 3,000,965.

* cited by examiner

AFFINITY CHROMATOGRAPHY CARRIER AND METHOD FOR PURIFYING BIOLOGICAL SUBSTANCE

CROSS-REFERENCE TO RELATED APPLICATIONS

This application is a Continuation of PCT International Application No. PCT/JP2016/081312 filed on Oct. 21, 2016, which claims priority under 35 U.S.C. § 119(a) to Japanese Patent Application No. 2015-208982 filed on Oct. 23, 2015. The above application is hereby expressly incorporated by reference, in its entirety, into the present application.

BACKGROUND OF THE INVENTION

1. Field of the Invention

The present invention relates to an affinity chromatography carrier and a method for purifying a biological substance.

2. Description of the Related Art

In recent years, along with the development of genetic engineering, protein engineering and cell engineering, development of drug utilizing functions of an antibody, which is called an antibody drug, has been actively conducted. As compared with a conventional drug, an antibody drug works more specifically on a target molecule, and it is therefore expected that use of an antibody drug will result in further reduced side effects and high therapeutic effects. In fact, an antibody drug contributes to improvements of various pathological conditions.

Meanwhile, since an antibody drug is administered to a living body in large amounts, the purity has a large influence on the quality of the antibody drug in the case of comparing with other recombinant protein drugs. Since an antibody drug is produced by purifying antibodies expressed in a host cell by genetic recombination, incorporation of impurities derived from host cells and production processes poses a problem. For example, since a host cell protein (HCP) remaining as an impurity in an antibody drug is assumed to be associated with the onset of anaphylaxis upon administration of the antibody drug, it is required that purification purity is improved to reduce impurities.

For example, WO2010/095673A discloses, as a chromatography carrier suitable for separation and purification of a protein preparation or the like, a chromatography carrier obtained by adding a sulfoxy group as a ligand to a porous cellulose-based gel constituted of porous cellulose particles with a polysaccharide having an intrinsic viscosity of 0.21 dL/g to 0.90 dL/g being added thereto, in which the dry weight per unit volume of the porous cellulose-based gel is 1.06 to 1.40 times the dry weight per unit volume of the porous cellulose particles.

Further, for example, WO2014/034457A discloses that an affinity chromatography carrier obtained by immobilizing an affinity ligand having a function of specifically binding to a specific molecule on a water-insoluble carrier is utilized for efficient separation and purification of useful substances from microorganisms and mammalian cell cultured cells containing biological components or recombinants and discloses an affinity chromatography carrier having an affinity ligand and a cation exchange group on the same carrier, as an affinity chromatography carrier achieving a high purification purity of antibodies.

SUMMARY OF THE INVENTION

However, the present inventors have examined the cation exchange chromatography carrier described in WO2010/095673A and found that there is room for improvement in the purification purity even though such a cation exchange chromatography carrier exhibits an excellent antibody adsorption capacity, as shown in Reference Example 1 described in the present specification.

In addition, the present inventors have examined the affinity chromatography carrier described in WO2014/034457A and found that an affinity chromatography carrier having an affinity ligand and a cation exchange group on the same carrier is thought to be advantageous, but, as shown in Comparative Examples 4 and 5 given in the present specification, there is room for improvement in the purification purity even though such an affinity chromatography carrier exhibits an excellent antibody adsorption capacity.

Therefore, it is an object of the present invention to provide an affinity chromatography carrier which exhibits an excellent antibody adsorption capacity and an excellent purification purity.

As a result of extensive studies to achieve the foregoing object, the present inventors have found that an affinity chromatography carrier having a substrate, a hydrophilic polymer, and an affinity ligand exhibits an excellent antibody adsorption capacity and an excellent purification purity, in the case where the substrate is constituted of at least one selected from the group consisting of a polysaccharide, an acrylate-based polymer, a methacrylate-based polymer and a styrene-based polymer, the hydrophilic polymer is at least one selected from the group consisting of hydrophilic polysaccharides, the affinity ligand is at least one selected from the group consisting of an antibody-binding protein and an antibody-binding polypeptide, a carboxy group is introduced into the affinity chromatography carrier, and the amount of the carboxy group introduced is 15 mmol/L-gel to 60 mmol/L-gel in terms of ion exchange capacity. The present invention has been completed based on these findings.

That is, the present invention provides the following [1] to [14].

[1] An affinity chromatography carrier, comprising:
a substrate;
a hydrophilic polymer; and
an affinity ligand, in which
the substrate is comprised of at least one selected from the group consisting of a polysaccharide, an acrylate-based polymer, a methacrylate-based polymer and a styrene-based polymer,
the hydrophilic polymer is at least one selected from the group consisting of hydrophilic polysaccharides,
the affinity ligand is at least one selected from the group consisting of an antibody-binding protein and an antibody-binding polypeptide,
a carboxy group is introduced into the affinity chromatography carrier, and
the amount of the carboxy group introduced is 15 mmol/L-gel to 60 mmol/L-gel in terms of ion exchange capacity.

[2] The affinity chromatography carrier according to [1], in which the hydrophilic polymer has an intrinsic viscosity of 0.10 dL/g or more.

[3] The affinity chromatography carrier according to [1] or [2], in which the coating amount of the hydrophilic polymer is 3 mg/g-dry gel to 500 mg/g-dry gel.

[4] The affinity chromatography carrier according to any one of [1] to [3], in which the substrate is comprised of at least one selected from the group consisting of a polysaccharide, an acrylate-based polymer and a methacrylate-based polymer.

[5] The affinity chromatography carrier according to any one of [1] to [4], in which the hydrophilic polymer is at least one selected from the group consisting of dextran, carboxymethyl dextran and pullulan.

[6] The affinity chromatography carrier according to any one of [1] to [5], in which the substrate is a porous particle.

[7] The affinity chromatography carrier according to any one of [1] to [6], in which the affinity ligand undergoes an antigen-antibody reaction with an antibody.

[8] The affinity chromatography carrier according to any one of [1] to [7], in which the affinity ligand is protein A or a variant thereof.

[9] The affinity chromatography carrier according to any one of [1] to [8], in which the substrate is comprised of at least one selected from the group consisting of cellulose, agarose, dextran, chitosan, glucomannan, and a crosslinked polysaccharide obtained by introducing a crosslinked structure thereinto, the hydrophilic polymer is at least one hydrophilic polysaccharide selected from the group consisting of dextran, carboxymethyl dextran and pullulan, the intrinsic viscosity of the hydrophilic polysaccharide is 0.12 dL/g to 0.30 dL/g, the coating amount of the hydrophilic polymer is 10 mg/g-dry gel to 240 mg/g-dry gel, the amount of the carboxy group introduced is 15 mmol/L-gel to 55 mmol/L-gel in terms of ion exchange capacity, the affinity ligand is protein A or a variant thereof, and the amount of the affinity ligand introduced is 0.10 mmol/L-gel to 1.0 mmol/L-gel.

[10] The affinity chromatography carrier according to any one of [1] to [8], in which the substrate is comprised of at least one selected from the group consisting of an acrylate-based polymer and a methacrylate-based polymer, the hydrophilic polymer is at least one hydrophilic polysaccharide selected from the group consisting of dextran, carboxymethyl dextran and pullulan, the intrinsic viscosity of the hydrophilic polysaccharide is 0.12 dL/g to 0.30 dL/g, the coating amount of the hydrophilic polymer is 10 mg/g-dry gel to 240 mg/g-dry gel, the amount of the carboxy group introduced is 15 mmol/L-gel to 55 mmol/L-gel in terms of ion exchange capacity, the affinity ligand is protein A or a variant thereof, and the amount of the affinity ligand introduced is 0.10 mmol/L-gel to 1.0 mmol/L-gel.

[11] A purification method for purifying a biological substance using the affinity chromatography carrier according to any one of [1] to [10].

[12] The purification method according to [11], in which the pH at the time of adding the biological substance is 5.0 to 9.0.

[13] The purification method according to [11] or [12], in which the pH at the time of eluting the biological substance is 2.0 to 5.0.

[14] The purification method according to any one of [11] to [13], in which the biological substance is an antibody or an antibody derivative.

According to the present invention, an affinity chromatography carrier exhibiting an excellent antibody adsorption capacity and an excellent purification purity is provided.

DESCRIPTION OF THE PREFERRED EMBODIMENTS

By a configuration in which the affinity chromatography carrier of the present invention has both an affinity ligand which is at least one selected from the group consisting of an antibody-binding protein and an antibody-binding polypeptide and a carboxy group which is a cation exchange group, and the amount of the carboxy group introduced is within the range of 15 mmol/L-gel to 60 mmol/L-gel in terms of ion exchange capacity, it was possible to reduce the amount of non-specific adsorption, and therefore improve the purification purity. In addition, the carboxy group has a lower ionic strength than the sulfoxy group, and is therefore advantageous because non-specific adsorption can be suppressed.

Hereinafter, the affinity chromatography carrier of the present invention and the production method thereof will be described in detail.

With respect to a numerical range, numerical values on the left and right of "to" are intended to be included in the numerical range.

[Affinity Chromatography Carrier]

The affinity chromatography carrier of the present invention is an affinity chromatography carrier including a substrate, a hydrophilic polymer, and an affinity ligand, in which the substrate is constituted of at least one selected from the group consisting of a polysaccharide, an acrylate-based polymer, a methacrylate-based polymer and a styrene-based polymer, the hydrophilic polymer is at least one selected from the group consisting of polysaccharides, the affinity ligand is at least one selected from the group consisting of an antibody-binding protein and an antibody-binding polypeptide, a carboxy group is introduced into the affinity chromatography carrier, and the amount of the carboxy group introduced is 15 mmol/L-gel to 60 mmol/L-gel in terms of ion exchange capacity.

<Substrate>

The substrate is at least one selected from the group consisting of a polysaccharide, an acrylate-based polymer, a methacrylate-based polymer and a styrene-based polymer, preferably at least one selected from the group consisting of a polysaccharide, an acrylate-based polymer and a methacrylate-based polymer, and more preferably at least one selected from polysaccharides. Also, one substrate may be used alone or two or more substrates may be used in combination.

The polysaccharide is not particularly limited, and examples thereof include natural polysaccharides such as cellulose, agarose, dextran, chitosan, and glucomannan, and crosslinked polysaccharides obtained by introducing a crosslinked structure into these natural polysaccharides. The crosslinked polysaccharide can be produced, for example, by introducing a crosslinked structure into the hydroxyl group of the natural polysaccharide using a crosslinking agent such as epichlorohydrin, (poly)alkylene glycol diglycidyl ether, or alkylene diisocyanate.

The polysaccharide is preferably at least one selected from cellulose, crosslinked cellulose, agarose and crosslinked agarose, and more preferably at least one selected from agarose and crosslinked agarose.

The acrylate-based polymer is not particularly limited, and examples thereof include a polymer obtained by polymerizing one kind of acrylic acid esters such as methyl acrylate, ethyl acrylate, hydroxyethyl acrylate, hydroxypropyl acrylate, butyl acrylate, stearyl acrylate, 2-ethylhexyl acrylate, cyclohexyl acrylate, glycerin monoacrylate, glycidyl acrylate, 4,5-epoxybutyl acrylate, and 9,10-epoxy stearyl acrylate; a copolymer obtained by copolymerizing two or more kinds of the foregoing acrylic acid esters; and a copolymer obtained by copolymerizing one or more kinds of acrylic acid esters with one or more kinds of vinyl group-containing compounds other than acrylic acid esters. Examples of vinyl group-containing compounds other than acrylic acid esters include a monovinyl compound such as ethylene or propylene, an aromatic polyvinyl compound such as divinylbenzene or trivinylbenzene, and a polyvinyl compound such as butadiene, methylenebisacrylamide, or triallyl isocyanurate. A crosslinking structure may be introduced into these polymers or copolymers using a crosslinking agent such as epichlorohydrin, (poly)alkylene glycol diglycidyl ether, or alkylene diisocyanate.

The methacrylate-based polymer is not particularly limited, and examples thereof include a polymer obtained by polymerizing one kind of methacrylic acid esters such as methyl methacrylate, ethyl methacrylate, hydroxyethyl methacrylate, hydroxypropyl methacrylate, butyl methacrylate, stearyl methacrylate, 2-ethylhexyl methacrylate, cyclohexyl methacrylate, glycerin monomethacrylate, glycidyl methacrylate, 4,5-epoxybutyl methacrylate, and 9,10-epoxy stearyl methacrylate; a copolymer obtained by copolymerizing two or more kinds of the foregoing methacrylic acid esters; and a copolymer obtained by copolymerizing one or more kinds of methacrylic acid esters with one or more kinds of vinyl group-containing compounds other than methacrylic acid esters. Examples of vinyl group-containing compounds other than methacrylic acid esters include a monovinyl compound such as ethylene or propylene, an aromatic polyvinyl compound such as divinylbenzene or trivinylbenzene, and a polyvinyl compound such as butadiene, methylenebisacrylamide, or triallyl isocyanurate. A crosslinking structure may be introduced into these polymers or copolymers using a crosslinking agent such as epichlorohydrin, (poly)alkylene glycol diglycidyl ether, or alkylene diisocyanate.

The styrene-based polymer is not particularly limited, and examples thereof include a polymer obtained by polymerizing one kind of styrene-based compounds such as styrene, methylstyrene, ethylstyrene, hydroxystyrene, and chlorostyrene; a copolymer obtained by copolymerizing two or more kinds of the foregoing styrene-based compounds; and a copolymer obtained by copolymerizing one or more kinds of styrene-based compounds with one or more kinds of vinyl group-containing compounds other than styrene-based compounds. Examples of vinyl group-containing compounds other than styrene-based compounds include a monovinyl compound such as ethylene or propylene, an aromatic polyvinyl compound such as divinylbenzene or trivinylbenzene, and a polyvinyl compound such as butadiene, methylenebisacrylamide, or triallyl isocyanurate. A crosslinking structure may be introduced into these polymers or copolymers using a crosslinking agent such as epichlorohydrin, (poly) alkylene glycol diglycidyl ether, or alkylene diisocyanate.

The substrate is preferably a porous particle or a porous film. Since the substrate is a porous particle or a porous film, the surface area thereof is increased and therefore the treatment capacity per unit time can be increased.

Although the pore volume of the substrate in the case where the substrate is a porous particle or a porous film is not particularly limited, the pore volume measured by a mercury porosimeter is preferably within the range of 0.2 mL/g to 10 mL/g and more preferably 0.2 mL/g to 5.0 mL/g. In the case where the pore volume is within this range, the antibody adsorption capacity and purification purity are improved. In addition, the mechanical strength does not decrease.

Although the specific surface area of the substrate in the case where the substrate is a porous particle or a porous film is not particularly limited, the specific surface area measured by a Brunauer, Emmett, Teller (BET) method (BET specific surface area) is preferably within the range of 2 $m^2/g$ to 1,500 $m^2/g$ and more preferably 5 $m^2/g$ to 1,000 $m^2/g$. In the case where the specific surface area is within this range, the antibody adsorption capacity and purification purity are improved.

The average particle diameter of the substrate in the case where the substrate is a porous particle is not particularly limited, but it is preferably within the range of 0.5 µm to 1,000 µm, more preferably 1 µm to 250 µm, and still more preferably 2 µm to 150 µm. In the case where the average particle diameter is within this range, the loss of pressure in the case of a column being filled with porous particles and then allowing a liquid to pass therethrough can be decreased and the flow rate of the liquid can be increased, which, in turn, results in an improved treatment efficiency as well as improved antibody adsorption capacity and purification purity. The average particle diameter of the porous particles can be measured by a known method. For example, an average particle diameter can be obtained by measuring particle diameters of 100 or more porous particles by an optical microscope and calculating the volume median diameter from the particle diameter distribution thereof.

Examples of commercially available products of the substrate include, but are not limited to, SEPHAROSE series (manufactured by GE Healthcare GmbH) which is an agarose-based carrier ("SEPHAROSE" is a registered trademark), CELLUFINE series (manufactured by JNC Corporation) which is a cellulose-based crosslinking carrier ("CELLUFINE" is a registered trademark), SEPHACRYL series (manufactured by GE Healthcare GmbH) which is a crosslinked polymer of allyl dextran and N,N'-methylenebisacrylamide ("SEPHACRYL" is a registered trademark), and TOYOPEARL HW series (manufactured by Tosoh Corporation) which is an acrylate-based carrier ("TOYOPEARL" is a registered trademark).

<Hydrophilic Polymer>

The hydrophilic polymer is at least one selected from the group consisting of hydrophilic polysaccharides. One hydrophilic polymer may be used alone or two or more hydrophilic polymers may be used in combination.

In the present invention, the term "hydrophilic" used in conjunction with a polymer or a polysaccharide refers to the fact that the polymer or polysaccharide contains at least one type of hydrophilic group. Preferred examples of the hydrophilic group include a functional group such as a carboxy group, an alkali metal salt of a carboxy group, a sulfoxy group, an alkali metal salt of a sulfoxy group, a hydroxy group, an amide group, a carbamoyl group, a sulfonamide group, a sulfamoyl group, a phosphoric group, an alkali metal salt of a phosphoric group, an oxyphosphoric group, and an alkali metal salt of an oxyphosphoric group. These hydrophilic groups may be present at any position in the polymer. For example, the hydrophilic group may be bonded to the polymer side chain directly or through a linking group, or may be bonded to the polymer side chain or the graft side chain. In addition, a plurality of hydrophilic groups are preferably present in one molecule.

The hydrophilic polysaccharide is not particularly limited, but it is preferably at least one selected from dextran, carboxymethyl dextran and pullulan and more preferably dextran, from the viewpoint of having a high effect of improving the purification purity.

Coating the substrate with a hydrophilic polymer increases the hydrophilicity of the surface of the affinity chromatography carrier of the present invention and suppresses adsorption of non-specific adsorbates, which thus has an effect of improving the purification purity.

The molecular weight of the hydrophilic polymer is not particularly limited, but it is preferably within the range of 0.10 dL/g or more, more preferably 0.10 dL/g to 0.90 dL/g, still more preferably 0.12 dL/g to 0.90 dL/g, even more preferably 0.12 dL/g to 0.30 dL/g, and even still more preferably 0.17 dL/g to 0.25 dL/g in terms of intrinsic viscosity. In the case where the intrinsic viscosity is within this range, the purification purity is further improved. The intrinsic viscosity can be determined by measuring the viscosity of polymer solutions of several different concentrations according to the viscosity measurement method in the general measurement method listed in the 16th revised Japanese Pharmacopoeia, the first method "capillary viscometer method" to measure the concentration dependence of the viscosity, and extrapolating the concentration of the obtained straight line to 0.

Meanwhile, the following Mark-Houwink-Sakurada equation is established between the intrinsic viscosity η and the molecular weight M of the polymer. Therefore, once the molecular weight of several samples is determined by using a direct measurement method, and K and α are determined from the molecular weight and the respective intrinsic viscosity values, the molecular weight M is determined by measuring the intrinsic viscosity η and the intrinsic viscosity η is determined by measuring the molecular weight M, respectively, for the same type of polymers.

$$\eta = KM^\alpha$$

Here, K and α are constants determined by the type of polymer, the type of solvent and the temperature.

For example, it is known that the intrinsic viscosity ($\eta_{Dextran}$) and the weight-average molecular weight ($Mw_{Dextran}$) of dextran satisfy the following relational expression.

$$\eta_{Dextran}[dL/g] = 9 \times 10^{-4} \times Mw_{Dextran}^{0.5}[dL/g]$$

The coating amount of the hydrophilic polymer (hereinafter, sometimes simply referred to as "hydrophilic polymer coating amount") is not particularly limited, but it is preferably 3 mg/g-dry gel to 500 mg/g-dry gel, more preferably 3 mg/g-dry gel to 350 mg/g-dry gel, still more preferably 10 mg/g-dry gel to 300 mg/g-dry gel, and even more preferably 20 mg/g-dry gel to 240 mg/g-dry gel. In the case where the hydrophilic polymer coating amount is within this range, the hydrophilicity of the surface of the affinity chromatography carrier of the present invention is moderately increased to thereby suppress adsorption of non-specific adsorbates and there is room for diffusion and penetration of antibodies into a substrate, thus increasing an antibody adsorption capacity, so that the purification purity is further improved. The hydrophilic polymer does not need to cover the entire surface of the substrate, and it is sufficient that the hydrophilic polymer covers at least a part of the substrate.

The hydrophilic polymer coating amount [unit: mg/g-dry gel] is calculated by dividing the dry weight ($W_P$) [unit: mg] of the coated hydrophilic polymer by the dry weight ($W_0$) [unit: g-dry gel] of the substrate before coating. The dry weight ($W_P$) of the hydrophilic polymer is the difference ($W_1 - W_0$) [unit: mg] between the dry weight ($W_1$) of the total amount of the carrier and the dry weight ($W_0$) of the substrate before coating.

Therefore, the hydrophilic polymer coating amount can be determined by the following equation.

Hydrophilic polymer coating amount (mg/g-dry gel) = $W_P / W_0 = (W_1 - W_0)/W_0$ The dry weight ($W_0$) of the substrate before coating can be calculated as follows.

$W_0 = W_{0,xg} \times w_0 / x$ in which $W_{0,xg}$: dry weight of wet gel xg of substrate before coating, $w_0$: wet gel total weight of substrate before coating used for hydrophilic polymer coating reaction, and x: wet gel weight (xg) of substrate before coating used for drying.

The dry weight ($W_1$) of the total amount of the carrier can also be calculated in the same manner.

<Affinity Ligand>

The affinity ligand is at least one selected from the group consisting of an antibody-binding protein and an antibody-binding polypeptide, and preferably at least one selected from antibody-binding proteins.

In the present invention, the polypeptide is a molecule containing a peptide chain consisting of 2 to 50 amino acid residues, and generally refers to a molecule having a molecular weight of less than 5,000. In the present invention, the protein is a molecule containing a peptide chain consisting of 51 or more amino acid residues, and generally refers to a molecule having a molecular weight of 5,000 or more.

The antibody-binding protein is not particularly limited as long as it is a protein that binds to an antibody by an antigen-antibody reaction, and examples thereof include protein A, protein G, protein L, protein D, and a variant of protein A. The antibody-binding protein is preferably protein A or a variant thereof. The variant of protein A is preferably an alkali-resistant protein A.

The antibody-binding polypeptide is not particularly limited as long as it is a polypeptide that binds to an antibody by an antigen-antibody reaction, and examples thereof include a polypeptide having an amino acid sequence identical to a part of the amino acid sequence of the antibody-binding domain of protein A and variants thereof. The variant of the antibody-binding polypeptide is preferably an alkali-resistant variant.

The amount of the affinity ligand to be introduced into the affinity chromatography carrier of the present invention (hereinafter, sometimes simply referred to as "affinity ligand introduction amount") is not particularly limited, but it is preferably 0.01 mmol/L-gel to 100 mmol/L-gel, more preferably 0.05 mmol/L-gel to 50 mmol/L-gel, still more preferably 0.10 mmol/L-gel to 10 mmol/L-gel, even more preferably 0.10 mmol/L-gel to 2.0 mmol/L-gel, further more preferably 0.10 mmol/L-gel to 1.0 mmol/L-gel, and even still more preferably 0.10 mmol/L-gel to 0.50 mmol/L-gel.

<Carboxy Group>

The amount of the carboxy group to be introduced into the affinity chromatography carrier of the present invention (hereinafter, sometimes simply referred to as "carboxy group introduction amount") is 15 mmol/L-gel to 60 mmol/L-gel, preferably 15 mmol/L-gel to 55 mmol/L-gel, and still more preferably 15 mmol/L-gel to 40 mmol/L-gel in terms of ion exchange capacity. In the case where the carboxy group introduction amount is within this range, the affinity ligand introduction amount can be set within an appropriate range, and therefore the antibody adsorption capacity is improved. In addition, adsorption of non-specific adsorbates can be suppressed.

[Method for Producing Affinity Chromatography Carrier]

The affinity chromatography carrier of the present invention can be produced by coating a substrate with a hydrophilic polymer, introducing a carboxy group thereinto, and further introducing an affinity ligand.

Details of the substrate, the hydrophilic polymer, and the affinity ligand are as described in the section "Affinity chromatography carrier".

<Coating with Hydrophilic Polymer>

The substrate is coated with a hydrophilic polymer.

The method of coating the substrate with a hydrophilic polymer is not particularly limited as long as it is capable of binding the hydrophilic polymer to the substrate by a covalent bond. Examples of the method of coating the substrate with a hydrophilic polymer include a method in which a substrate is reacted with chloromethyloxirane (epichlorohydrin) to introduce an epoxy group into the substrate which is then reacted with a hydrophilic polymer; a method in which a substrate is reacted with a crosslinking agent such as chloromethyloxirane (epichlorohydrin) in the presence of an alkali in a solvent, and the resulting reaction product is reacted with a hydrophilic polymer; and a method in which a halogen group such as a chloro group is introduced into a substrate using a halogenating agent and a hydrophilic polymer is immobilized on the substrate using Williamson ether synthesis.

In the case where the substrate is coated with the hydrophilic polymer, the hydrophilic polymer coating amount is preferably 3 mg/g-dry gel to 500 mg/g-dry gel, more preferably 3 mg/g-dry gel to 350 mg/g-dry gel, still more preferably 10 mg/g-dry gel to 300 mg/g-dry gel, and even more preferably 20 mg/g-dry gel to 240 mg/g-dry gel.

In the present specification, a substrate immediately before coating with a hydrophilic polymer is sometimes referred to as "substrate before coating" in some cases, and a product obtained by coating such a substrate before coating with a hydrophilic polymer is sometimes referred to as "carrier" in some cases.

<Introduction of Carboxy Group>

A carboxy group is introduced into a carrier.

The method of introducing a carboxy group into the carrier is not particularly limited as long as it is capable of binding a compound having a carboxy group to the carrier by a covalent bond. Examples of the method of introducing a carboxy group into the carrier include a method in which a carrier is reacted with chloroacetic acid under alkaline conditions and a carboxymethyl group is introduced into a part of hydroxy groups on the surface of the carrier; and a method in which an aldehyde group is introduced into a carrier, and a carboxy group is introduced into the aldehyde group by reductive amination through an amino group of a compound having a carboxy group and an amino group such as amino acid.

In the case of introducing a carboxy group into the carrier, the amount of the carboxy group introduced is 15 mmol/L-gel to 60 mmol/L-gel, preferably 15 mmol/L-gel to 55 mmol/L-gel, and more preferably 15 mmol/L-gel to 40 mmol/L-gel in terms of ion exchange capacity.

In the present specification, the product obtained by introducing a carboxy group into the carrier is sometimes referred to as "carboxylated carrier" in some cases.

<Introduction of Affinity Ligand>

An affinity ligand is introduced (immobilized) into the carboxylated carrier.

The method of introducing (immobilizing) an affinity ligand into the carboxylated carrier is not particularly limited as long as it is capable of binding the affinity ligand to the carboxylated carrier by a covalent bond. Examples of the method of introducing (immobilizing) an affinity ligand into the carboxylated carrier include a method in which a part of carboxy groups is converted into N-(3-dimethylaminopropyl)-N'-ethylcarbodiimide (EDC)/N-hydroxysuccinimide (NHS) and reacted with an affinity ligand such as protein A, and the unreacted EDC/NHS-converted carboxy group is regenerated after the reaction; and a method in which, in the case of an affinity ligand having an amino group such as protein A, a carboxy group is protected, an aldehyde group is introduced, and then the affinity ligand is introduced into the aldehyde group by reductive amination through an amino group.

In the case where the affinity ligand is introduced into the carboxylated carrier, the amount of the affinity ligand introduced is preferably 0.01 mmol/L-gel to 100 mmol/L-gel, more preferably 0.05 mmol/L-gel to 50 mmol/L-gel, still more preferably 0.10 mmol/L-gel to 10 mmol/L-gel, even more preferably 0.10 mmol/L-gel to 2.0 mmol/L-gel, even further preferably 0.10 mmol/L-gel to 1.0 mmol/L-gel, and even still more preferably 0.10 mmol/L-gel to 0.50 mmol/L-gel.

In the case where the affinity ligand is bonded to a part of the carboxy group of the carboxylated carrier, the amount of the carboxy group introduced into the affinity chromatography carrier is expressed by "amount of carboxy group introduced into carboxylated carrier–amount of affinity ligand introduced into affinity chromatography carrier".

[Method for Purifying Biological Substance and Biological Substance Purified by Same Purification Method]

<Biological Substance>

The biological substance to be purified by the affinity chromatography carrier of the present invention is not particularly limited, but it is preferably an antibody or an antibody derivative and more preferably immunoglobulin G or a derivative thereof.

The antibody refers to an immunoglobulin or an analog, fragment or fusion thereof. Here, the analog refers to a naturally occurring or artificially constructed protein or protein conjugate in which the structure or function of the immunoglobulin is at least partially retained. The fragment refers to a protein having a partial structure of the immunoglobulin which is constructed by enzymatic treatment or genetic engineering design. In addition, the fusion includes Fc fusion proteins (Fc-containing molecules) obtained by fusing a Fragment crystallizable (Fc) region, which is a constant region of an immunoglobulin molecule, with other functional proteins or peptides. In the present invention, the immunoglobulin may be any of the five classes (isotypes) of Immunoglobulin G (IgG), Immunoglobulin M (IgM), Immunoglobulin A (IgA), Immunoglobulin D (IgD), and Immunoglobulin E (IgE), but it is preferably IgG or IgM and more preferably IgG.

The antibody derivative refers to a chimeric antibody in which an Fc region of a human immunoglobulin and an Fab region of a non-human mammalian immunoglobulin are fused, a chimeric antibody in which several Fc regions of a human immunoglobulin and several Fv regions of a non-human mammalian immunoglobulin are fused, a humanized antibody in which the remaining portion excluding a complementarity determining region (CDR) portion of a human immunoglobulin and a non-human mammalian immunoglobulin CDR portion are fused, a chimeric antibody in which an Fc region of a non-human mammal immunoglobulin and a Fragment, antigen binding (Fab) region of a human immunoglobulin are fused, a chimeric antibody in which several Fc regions of a non-human mammal immunoglobulin and several Fv regions of a human immunoglobulin are fused, a non-human mammalian antibody in which the remaining portion excluding a CDR portion of a human immunoglobulin and a CDR portion of a non-human mammalian immunoglobulin are fused, a chimeric antibody in which an Fc region of a non-human mammal immunoglobulin and an Fab region of a non-human mammalian immunoglobulin are fused, a chimeric antibody in which several Fc regions of a non-human mammalian immunoglobulin and several Fv regions of a non-human mammalian immunoglobulin are fused, a non-human mammalian antibody in which the remaining portion excluding a complementarity determining region (CDR) portion of a non-human mammalian immunoglobulin and a non-human mammalian immunoglobulin CDR portion are fused, or a chemically modified protein thereof which retains an Fc region.

These antibody proteins are used as raw materials for antibody drugs.

<Purification Method>

Hereinafter, a detailed description of the purification method using the affinity chromatography carrier of the present invention is exemplified for the case where the biological substance is immunoglobulin G, but the present invention is not limited thereto.

The purification of a biological substance (in particular, an antibody) using an affinity chromatography carrier is largely composed of four steps of an adsorption step, a washing step, an ionic strength adjusting step, and an elution step, and may include subsequent steps for re-use such as a regeneration step and/or a cleaning-in-place (CIP) step, and a re-equilibration step.

In the adsorption step, a general affinity chromatography purification method can be used. That is, in one example, the pH of a protein solution containing immunoglobulin G is adjusted to near neutral pH and then the solution is passed through a column packed with the affinity chromatography carrier of the present invention, so that the immunoglobulin G is specifically adsorbed on the affinity chromatography carrier through an affinity ligand. For example, in the case where protein A is used as the affinity ligand, the loading pH, that is, the pH at the time of adding a biological substance is preferably 5.0 to 9.0, more preferably 5.3 to 9.0, still more preferably 5.5 to 9.0, and even more preferably 6.0 to 8.5. In the purification of immunoglobulin G produced by cultured mammalian cells, it is not necessary to specifically adjust the ionic strength, and it is also possible to further suppress the non-specific adsorption by increasing the ionic strength in advance.

In the washing step, an appropriate amount of a buffer solution within the range of conditions in which the affinity ligand functions is allowed to pass, so that the interior of the column is washed. That is, the preferred range of the pH may be the same range as that at the time of loading. For example, it is preferably a pH of 5.0 to 9.0. At this point, the immunoglobulin G is adsorbed on the affinity chromatography carrier of the present invention. In this case, impurities may be effectively removed by optimizing ionic strength and composition at a pH near neutral. It is preferred that the carboxy group does not function at the time of washing, that is, it is preferable to use a washing solution having a certain ionic strength or more at a pH near neutral, and in this process, it is possible to wash impurities non-specifically remaining in the column through the affinity chromatography carrier and/or the immunoglobulin G. The ionic strength is, for example, preferably 0.2 M or more and more preferably 0.5 M or more.

In the ionic strength adjusting step, the column is replaced with a buffer solution having a low ionic strength near neutrality to prepare for the expression of an ionic strength-dependent elution function by the carboxy group at the time of elution.

In the elution step, the combination of acidic pH and ionic strength allows the cation exchange separation mode to function at the time of elution from the affinity ligand, and therefore a fraction having a high monomer content can be recovered into a low ionic strength elution fraction by the cooperative action of both ligands. As for the pH of the eluate, the pH at the time of elution of immunoglobulin G from the affinity ligand can be applied. Since this pH is determined mainly by the separation conditions determined by the affinity chromatography carrier and the type of immunoglobulin G, it is not necessary to set special conditions.

In the case where protein A is used as the affinity ligand, the pH at the time of elution is preferably set to 2.0 to 5.0. However, for the purpose of avoiding acid denaturation of the biological substance, the pH is more preferably pH 2.8 or more, still more preferably pH 3.0 or more, and even more preferably pH 3.2 or more. The pH is preferably 5.0 or less and more preferably 4.8 or less.

In the case where an alkaline-resistant protein A is used as the affinity ligand, the pH at the time of elution is generally set to preferably 3.5 to 4.0, but it is not limited thereto. In addition, the elution ionic strength depends on the introduction ratio of the affinity ligand and the carboxy group and also depends on the loading amount of immunoglobulin G per unit volume, but the optimization point thereof can be easily set by gradient experiment or stepwise dissolution experiment.

The antibody elution from the affinity chromatography carrier prepared according to the present invention can be applied either by salt concentration gradient elution or stepwise elution, but in the case of aiming to reduce the amount of eluate, stepwise elution by ionic strength is preferable. Further, in order to simplify the operation, it is preferable to set the conditions that can achieve recovery and high purification purity of antibodies by one step elution.

Even with a combination of ionic strength and acidic pH in the washing step, in the case where the aggregate remains in the column and does not incorporate into the eluted fraction, the ionic strength adjusting step can be omitted.

<Purified Biological Substance>

The biological substance purified according to the purification method of the present invention, particularly an antibody or an antibody derivative, exhibits an increased purification purity although the structure and properties of the biological substance are not changed before and after purification thereof. However, since the purification purity depends on the solution or the like before purification, it is impossible to say unconditionally how high the purification purity is.

The immunoglobulin G purified using the affinity chromatography carrier prepared according to the present invention exhibits a higher monomer selectivity than affinity chromatography carrier based on a single separation mode and a high content of monomers in the eluate.

Even in the case where an affinity chromatography carrier based on a single separation mode is used, it is possible to increase the monomer content to some extent by optimization of pH and ionic strength at the time of elution, but such an effect is low and it is accompanied by a greater decrease in recovery rate for exhibiting the effect. By using the affinity chromatography carrier of the present invention, since affinity purification with high specificity and improvement in monomer content that can be achieved mainly by cation exchange chromatography can be achieved with efficiency in a single chromatographic operation while maintaining a high recovery rate, it is possible to reduce the load on subsequent processes, which is therefore capable of contributing to improvement of the yield of the entire process and improvement of the monomer content. That is, the use of the novel affinity chromatography carrier of the present invention can contribute to improvement in productivity and purification of the antibody drug production process.

EXAMPLES

Hereinafter, the present invention will be described in more detail with reference to Examples, but the present invention is not limited thereto.

[Measurement Method and Evaluation Method]

1. Method for measuring hydrophilic polymer coating amount 5 g of the wet gel of a substrate before coating was dried at 50° C. under reduced pressure until the weight change disappeared and the weight thereof was measured, and the resulting numerical value from the product of the thus measured weight and the wet gel weight of the substrate before coating used for a hydrophilic polymer coating reaction was taken as the dry weight of the substrate before coating. Next, 5 g of the wet gel of a carrier obtained by coating the substrate before coating with a hydrophilic polymer was dried at 50° C. under reduced pressure until the weight change disappeared and the weight thereof was measured, and the resulting numerical value from the product of the thus measured weight and the wet gel weight of the carrier obtained after the hydrophilic polymer coating reaction was taken as the dry weight of the carrier. The difference between the dry weight of the carrier and the dry weight of the substrate before coating was taken as the dry weight of the hydrophilic polymer coating the substrate before coating. The hydrophilic polymer coating amount was calculated as the dry weight of the hydrophilic polymer per dry weight of the substrate before coating.

2. Method for measuring carboxy group introduction amount 1 g of the carboxylated carrier was suspended in 3 mL of pure water, the resulting suspension was poured into a disposable column having an inner diameter of 15 mm, and the solvent was removed by suction filtration. This was followed by washing 4 times with 3 mL of 0.2 mol/L hydrochloric acid and then repeated washing with 4 mL of pure water. After washing, the height of the bed (carrier part deposited on the column) was measured to calculate the volume of the carboxylated carrier. The carboxylated carrier was taken out, transferred to a 100 mL beaker, suspended in 40 mL of 0.1 mol/L saline, and titrated with a 0.1 mol/L aqueous sodium hydroxide solution using an automatic titrator "COM-1600" (manufactured by Hiranuma Sangyo Co., Ltd.). The ion exchange capacity (meq/L-gel) per 1 L of the carboxylated carrier was calculated from the amount of the titration solution up to the end point. Further, the unit was converted into "mmol/L-gel" (1 meq/L-gel=1 mmol/L-gel). The carboxy group introduction amount was expressed in terms of ion exchange capacity.

3. Method for Measuring Affinity Ligand Introduction Amount (Protein A Immobilization Amount)

The protein A solution, the reaction solution, and the washing solution after the protein A immobilization reaction were each subjected to gel filtration chromatography (which will be described below), and the amount of protein A contained in each solution was calculated from the peak surface area value of absorbance at 280 nm.

The protein A immobilization amount was calculated from the difference between the thus calculated amount of protein A and the amount of protein A contained in the protein A solution, the reaction solution, and the washing solution before the protein A immobilization reaction.

(Conditions for Gel Filtration Chromatography)

Chromatographic system: AKTA avant 25 (manufactured by GE Healthcare GmbH) ("AKTAavant" is a registered trademark)

Column: Desalting column "HiTrap Desalting" (manufactured by GE Healthcare GmbH) ("HITRAP" is a registered trademark)

Buffer: 20 mM phosphate buffer, 150 mM NaCl, pH 7.4

Flow rate: 3 mL/min

4. Evaluation Method of Antibody Adsorption Capacity (1) Measurement of Antibody Adsorption Capacity 1 mL of an affinity chromatography carrier prepared in Examples, a chromatography carrier prepared in Comparative Examples, or a commercially available chromatography carrier was packed in a glass column "TRICORN 10/20 column" (manufactured by GE Healthcare GmbH) ("TRICORN" is a registered trademark) which was then connected to a chromatography system "AKTA avant 25" (manufactured by GE Healthcare GmbH) ("AKTAavant" is a registered trademark), followed by the measurement of antibody adsorption capacity.

After the column was equilibrated with an equilibration solution (20 mM phosphate buffer, 150 mM NaCl, pH 7.4), 15 mL of a solution prepared by adjusting a human IgG antibody (Immunoglobulin G) to 5 mg/mL with standard buffer (20 mM phosphate buffer, 150 mM NaCl, pH 7.4) was added thereto at a flow rate of 0.42 mL/min. After washing the column with 5 mL of a post-loading washing solution (20 mM phosphate buffer, 150 mM NaCl, pH 7.4) at the same flow rate, 5 mL of a pre-elution washing solution (20 mM phosphate buffer, 1 M NaCl, pH 7.4) was allowed to flow at the same flow rate. Thereafter, 5 mL of an eluant (100 mM citrate buffer, 150 mM NaCl, pH 3.2) was allowed to flow at the same flow rate. Further continuously, 5 mL of a cleaning in place (CIP) solution (0.1 M aqueous sodium hydroxide solution) was allowed to flow at the same flow rate and then 5 mL of a re-equilibration solution (20 mM phosphate buffer, 150 mM NaCl, pH 7.4) was allowed to flow at the same flow rate. At this time, the antibody elution amount of the eluate in each fraction was calculated from the IgG elution peak obtained by monitoring the absorbance at 280 nm. The amount of antibodies eluted from the pre-elution washing solution to the CIP solution was calculated as the antibody adsorption capacity.

(2) Evaluation of Antibody Adsorption Capacity

The antibody adsorption capacity was evaluated based on the antibody adsorption capacity in the case where only a carboxy group and protein A were introduced, according to the following evaluation standards. That is, the antibody adsorption capacity was evaluated based on Comparative Example 4 for Examples 1 to 7, Comparative Examples 1 to 6 and 8 and Reference Example 1 (Examples, Comparative Examples and Reference Example in which the substrate was a polysaccharide), and based on Comparative Example 7 for Example 8 and Comparative Example 7 (Example and Comparative Example in which the substrate is a methacrylate-based polymer), respectively.

Antibody adsorption capacity is 40% or more of the standard Evaluation of antibody adsorption capacity "A"

Antibody adsorption capacity is less than 40% of the standard Evaluation of antibody adsorption capacity "C"

5. Evaluation Method of Purification Purity (1) Calculation of Purified Purity 1 mL of an affinity chromatography carrier prepared in Examples or Comparative Examples or a commercially available chromatography carrier was packed in a glass column "TRICORN 10/20 column" (manufactured by GE Healthcare GmbH) ("TRICORN" is a registered trademark) which was then connected to a chromatographic system "AKTA avant 25" (manufactured by GE Healthcare GmbH) ("AKTAavant" is a registered trademark), followed by the measurement of the amount of host cell protein (HCP) and the amount of Immunoglobulin G (IgG) eluted from each fraction.

After the column was equilibrated with an equilibration solution (20 mM phosphate buffer, 150 mM NaCl, pH 7.4), an IgG/HCP mixed solution prepared by using standard buffer (20 mM phosphate buffer, 150 mM NaCl, pH 7.4), so that IgG and HCP derived from a Chinese Hamster Ovary S (CHO-S) cell were 1.6 mg/mL and 0.32 mg/mL, respectively, was added at a flow rate of 0.21 mL/min such that an antibody amount of 80% of the antibody adsorption capacity obtained in the above (1) was loaded. After washing the column with 5 mL of a post-loading washing solution (20 mM phosphate buffer, 150 mM NaCl, pH 7.4) at a flow rate of 0.42 mL/min, 5 mL of a pre-elution washing solution (20 mM phosphate buffer, 1 M NaCl, pH 7.4) was allowed to flow at the same flow rate. Thereafter, 5 mL of an eluant (100 mM citrate buffer, 150 mM NaCl, pH 3.2) was allowed to flow at the same flow rate. Further continuously, 5 mL of a CIP solution (0.1 M aqueous sodium hydroxide solution) was allowed to flow at the same flow rate and then 5 mL of a re-equilibration solution (20 mM phosphate buffer, 150 mM NaCl, pH 7.4) was allowed to flow at the same flow rate. At this time, the IgG elution amount of the eluate in each fraction was calculated from the IgG elution peak obtained by monitoring the absorbance at 280 nm. The eluate of each fraction was recovered and the amount of HCP of the eluate in each fraction was calculated by ELISA using a host cell protein detection kit "CHO HCP 3rd Generation ELISA kit" (manufactured by Cygnus Technologies, Inc.).

Using the thus calculated IgG amount and HCP amount of the eluate, the purification purity was calculated according to the following equation in terms of HCP incorporation amount in the eluate, that is, HCP amount per IgG amount in the eluate.

Purification purity (ppm)=HCP incorporation amount (ppm)=HCP amount of eluate/IgG amount of eluate (2) Evaluation of Purification Purity The purification purity was evaluated based on the incorporated amount of HCP (ppm) in the case where only a carboxy group and protein A were introduced, according to the following evaluation standards. That is, the HCP incorporation amount was evaluated based on Comparative Example 4 for Examples 1 to 7, Comparative Examples 1 to 6 and 8 and Reference Example 1 (Examples, Comparative Examples and Reference Example in which the substrate was a polysaccharide), and based on Comparative Example 7 for Example 8 and Comparative Example 7 (Example and Comparative Example in which the substrate is a methacrylate-based polymer), respectively.

HCP incorporation amount (ppm) decreased by 20% or more Evaluation of purification purity "A"

HCP incorporation amount (ppm) decreased by more than 0% and less than 20% Evaluation of purification purity "B"

HCP incorporation amount (ppm) did not decrease Evaluation of purification purity "C"

Example 1

1. Preparation of Affinity Chromatography Carrier (1) Preparation of Wet Gel

The crosslinked agarose-based substrate, Sepharose 6 Fast Flow (manufactured by GE Healthcare GmbH) ("SEPHAROSE" is a registered trademark) was washed on a glass filter by repeating suspension and filtration using pure water, thereby obtaining a substrate slurry. The pure water was removed from the substrate slurry by suction filtration to obtain a wet gel.

In the column "Substrate" of Table 1, "Sepharose 6 FF" refers to "Sepharose 6 Fast Flow".

(2) Preparation of Substrate Before Coating—Introduction of Epoxy Group 100 g of the obtained wet gel, 152 mL of pure water and 50 g of chloromethyl oxirane were placed in a 500 mL three-neck flask and stirring of the contents of the flask was started in a warm bath at 45° C. Stirring was carried out until the temperature in the flask reached 45° C. 41 g of a 50% (w/w) aqueous sodium hydroxide solution was added dropwise in the flask over 2 hours in a warm bath at 45° C. while maintaining the temperature in the flask at about 45° C. After the whole amount of the aqueous sodium hydroxide solution was added dropwise, the mixture was further reacted for 1 hour and washed on a glass filter by repeating suspension and filtration using pure water to obtain a wet gel of the substrate before coating.

(3) Preparation of Carrier—Coating with Hydrophilic Polymer 13 g of dextran 70 (intrinsic viscosity: 0.23 dL/g; weight-average molecular weight: about 70,000) and 154 mL of pure water were placed in a 500 mL three-neck flask and stirring of contents of the flask was started at room temperature. Stirring was carried out until the dextran 70 was completely dissolved. After dissolution, 90 g of the wet gel of the substrate before coating was added to the three-neck flask which was then further stirred at room temperature. After the mixed solution in the three-neck flask became homogeneous, 4.2 g of a 50% (w/w) aqueous sodium hydroxide solution was added thereto. After adding the aqueous sodium hydroxide solution, the mixed solution was reacted at room temperature for 16 hours and washed on a glass filter by repeating suspension and filtration using pure water to obtain a wet gel of the carrier.

Further, the dextran coating amount of the obtained carrier was measured in accordance with the section "Method for measuring hydrophilic polymer coating amount" described above. The obtained hydrophilic polymer coating amount is shown in the column "Hydrophilic polymer coating amount" of Table 1.

(4) Preparation of Carboxylated Carrier—Introduction of Carboxy Group 12 g of the wet gel of the obtained carrier, 6.2 g of sodium chloroacetate and 24 mL of pure water were placed in a 100 mL three-neck flask and stirring of the contents of the flask was started in a warm bath at 50° C. Stirring was carried out until the sodium chloroacetate was completely dissolved. After dissolution, 8.8 g of a 50% (w/w) aqueous sodium hydroxide solution was added dropwise over 1 hour in a warm bath at 50° C. while maintaining the temperature in the flask at about 50° C. After the whole amount of the aqueous sodium hydroxide solution was added dropwise, the mixture was further reacted for 3 hours and washed on a glass filter by repeating suspension and filtration using pure water to obtain a wet gel of the carboxylated carrier.

Further, the carboxy group introduction amount of the obtained carboxylated carrier was measured in accordance with the section "Method for measuring carboxy group introduction amount" described above. The obtained carboxy group introduction amount is shown in the column "Carboxy group introduction amount" of Table 1.

The amount of carboxy group introduced into the affinity chromatography carrier was expressed in terms of "carboxy group introduction amount of carboxylated carrier–affinity ligand introduction amount".

(5) Preparation of Protein A-Immobilized Carboxylated Carrier—Introduction of Affinity Ligand The obtained carboxylated carrier was placed in a disposable column in an amount of 2.5 mL as a wet volume and washed by repeating suspension and filtration using pure water to obtain a carrier slurry. The pure water was removed from the carrier slurry by suction filtration to obtain a wet gel.

2.0 g of the obtained wet gel was placed in a reaction vessel and 2 mL of a solution of N-(3-dimethylaminopropyl)-N'-ethylcarbodiimide (EDC) was added thereto. The mixture was stirred with inversion of the reaction vessel at room temperature for 10 minutes. Thereafter, 2 mL of a solution of N-hydroxysuccinimide (NHS) was added to the reaction vessel which was then stirred with inversion thereof at room temperature for 30 minutes. Here, the EDC solution was prepared by dissolving 0.2 g of EDC in 2 mL of dimethyl sulfoxide (DMSO), and the NHS solution was prepared by dissolving 0.2 g of NHS in 2 mL of DMSO.

The reaction gel solution was transferred to a disposable column and washed with 6 mL of ice-cooled 1 mM hydrochloric acid to obtain an EDC/NHS activated carboxylated carrier.

1.5 g of the obtained EDC/NHS activated carboxylated carrier was placed in a reaction vessel, followed by addition of 1.5 mL of a 10 mg/mL protein A solution to the reaction vessel and shaking at 25° C. for 2 hours. The 10 mg/mL protein A solution was prepared by dissolving recombinant native protein A "rSPA" (manufactured by Repligen Corporation) in 20 mM 2-(N-morpholino)ethanesulfonic acid (MES) buffer (pH 4.5).

The solvent was replaced with a 1 M aqueous sodium chloride solution and a 0.5 M aqueous ethanolamine solution, followed by washing to obtain a protein A-immobilized carboxylated carrier.

In addition, the protein A immobilization amount (affinity ligand introduction amount) of the protein A-immobilized carboxylated carrier thus obtained was measured in accordance with the section "Method for measuring affinity ligand introduction amount (protein A immobilization amount)" described above. The protein A immobilization amount thus obtained is shown in the column "Affinity ligand introduction amount" of Table 1.

2. Evaluation of Antibody Adsorption Capacity and Purification Purity

Using the protein A-immobilized carboxylated carrier thus prepared, the antibody adsorption capacity and purification purity were evaluated in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Example 2

1. Preparation of Affinity Chromatography Carrier

A protein A-immobilized carboxylated carrier was prepared in the same manner as in Example 1, except that the amount of sodium chloroacetate used was changed from 6.2 g to 3.6 g at the time of preparing the carboxylated carrier (introduction of a carboxy group).

Further, the hydrophilic polymer coating amount, the carboxy group introduction amount, and the affinity ligand introduction amount were measured in the same manner as in Example 1. The measurement results are shown in the columns "Hydrophilic polymer coating amount", "Carboxy group introduction amount", and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Example 3

1. Preparation of Affinity Chromatography Carrier

A protein A-immobilized carboxylated carrier was prepared in the same manner as in Example 1, except that the amount of sodium chloroacetate used was changed from 6.2 g to 11.7 g at the time of preparing the carboxylated carrier (introduction of a carboxy group).

Further, the hydrophilic polymer coating amount, the carboxy group introduction amount, and the affinity ligand introduction amount were measured in the same manner as in Example 1. The measurement results are shown in the columns "Hydrophilic polymer coating amount", "Carboxy group introduction amount", and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Example 4

1. Preparation of Affinity Chromatography Carrier

A protein A-immobilized carboxylated carrier was prepared in the same manner as in Example 1, except that the amount of dextran 70 (intrinsic viscosity: 0.23 dL/g; weight-average molecular weight: about 70,000) used was changed from 13 g to 66 g at the time of preparing the carrier (coating with a hydrophilic polymer), and the amount of sodium chloroacetate used was changed from 6.2 g to 2.0 g at the time of preparing the carboxylated carrier (introduction of a carboxy group).

Further, the hydrophilic polymer coating amount, the carboxy group introduction amount, and the affinity ligand introduction amount were measured in the same manner as in Example 1. The measurement results are shown in the columns "Hydrophilic polymer coating amount", "Carboxy group introduction amount", and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Example 5

1. Preparation of Affinity Chromatography Carrier

A protein A-immobilized carboxylated carrier was prepared in the same manner as in Example 4, except that the crosslinked agarose-based substrate was changed to "Sepharose 4 Fast Flow" (manufactured by GE Healthcare GmbH) ("SEPHAROSE" is a registered trademark) at the time of preparing the wet gel, and the amount of sodium chloroacetate used was changed from 2.0 g to 3.9 g at the time of preparing the carboxylated carrier (introduction of a carboxy group).

In the column "Substrate" of Table 1, "Sepharose 4 FF" refers to "Sepharose 4 Fast Flow".

Further, the hydrophilic polymer coating amount, the carboxy group introduction amount, and the affinity ligand introduction amount were measured in the same manner as in Example 1. The measurement results are shown in the columns "Hydrophilic polymer coating amount", "Carboxy group introduction amount", and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Example 6

1. Preparation of Affinity Chromatography Carrier

A protein A-immobilized carboxylated carrier was prepared in the same manner as in Example 5, except that dextran 40 (intrinsic viscosity: 0.17 dL/g; weight-average molecular weight: about 40,000) was used in place of dextran 70 (intrinsic viscosity: 0.23 dL/g; weight-average molecular weight: about 70,000) at the time of preparing the carrier (coating with a hydrophilic polymer), and the amount of sodium chloroacetate used was changed from 3.9 g to 4.5 g at the time of preparing the carboxylated carrier (introduction of a carboxy group).

Further, the hydrophilic polymer coating amount, the carboxy group introduction amount, and the affinity ligand introduction amount were measured in the same manner as in Example 1. The measurement results are shown in the columns "Hydrophilic polymer coating amount", "Carboxy group introduction amount", and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Example 7

1. Preparation of Affinity Chromatography Carrier

A protein A-immobilized carboxylated carrier was prepared in the same manner as in Example 5, except that dextran 19 (intrinsic viscosity: 0.12 dL/g; weight-average molecular weight: about 19,000) was used in place of dextran 70 (intrinsic viscosity: 0.23 dL/g; weight-average molecular weight: about 70,000) at the time of preparing the carrier (coating with a hydrophilic polymer), and the amount of sodium chloroacetate used was changed from 3.9 g to 5.7 g at the time of preparing the carboxylated carrier (introduction of a carboxy group).

Further, the hydrophilic polymer coating amount, the carboxy group introduction amount, and the affinity ligand introduction amount were measured in the same manner as in Example 1. The measurement results are shown in the columns "Hydrophilic polymer coating amount", "Carboxy group introduction amount", and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Example 8

1. Preparation of Affinity Chromatography Carrier (1) Preparation of Wet Gel

A methacrylate-based porous substrate, "TOYOPEARL HW-65F (manufactured by Tosoh Corporation) ("TOYOPEARL" is a registered trademark) was washed on a glass filter by repeating suspension and filtration using pure water, thereby obtaining a substrate slurry. The pure water was removed from the substrate slurry by suction filtration to obtain a wet gel.

(2) Preparation of Substrate Before Coating—Introduction of Epoxy Group 100 g of the obtained wet gel, 152 mL of pure water and 50 g of chloromethyl oxirane were placed in a 500 mL three-neck flask and stirring of the contents of the flask was started in a warm bath at 45° C. Stirring was carried out until the temperature in the flask reached 45° C. 41 g of a 50% (w/w) aqueous sodium hydroxide solution was added dropwise in the flask over 2 hours in a warm bath at 45° C. while maintaining the temperature in the flask at about 45° C. After the whole amount of the aqueous sodium hydroxide solution was added dropwise, the mixture was further reacted for 1 hour and washed on a glass filter by repeating suspension and filtration using pure water to obtain a wet gel. By repeating this reaction three times, a wet gel of the substrate before coating was obtained.

(3) Preparation of Carrier—Coating with Hydrophilic Polymer

A wet gel of the carrier was obtained in the same manner as in Example 1, except that 126 g of dextran 40 (intrinsic viscosity: 0.17 dL/g; weight-average molecular weight: about 40,000) was used in place of 13 g of dextran 70 (intrinsic viscosity: 0.23 dL/g; weight-average molecular weight: about 70,000).

Further, the dextran coating amount of the obtained carrier was measured in the same manner as in Example 1, in accordance with the section "Method for measuring hydrophilic polymer coating amount" described above. The obtained hydrophilic polymer coating amount is shown in the column "Hydrophilic polymer coating amount" of Table 1.

(4) Preparation of Carboxylated Carrier—Introduction of Carboxy Group

A wet gel of a carboxylated carrier was obtained in the same manner as in Example 1 except that the amount of sodium chloroacetate used was changed from 6.2 g to 3.4 g.

Further, the carboxy group introduction amount of the obtained carboxylated carrier was measured in the same manner as in Example 1, in accordance with the section "Method for measuring carboxy group introduction amount" described above. The obtained carboxy group introduction amount is shown in the column "Carboxy group introduction amount" of Table 1.

(5) Preparation of Protein A-Immobilized Carboxylated Carrier—Introduction of Affinity Ligand A protein A-immobilized carboxylated carrier was obtained in the same manner as in Example 1.

In addition, the protein A immobilization amount of the protein A-immobilized carboxylated carrier thus obtained was measured in the same manner as in Example 1, in accordance with the section "Method for measuring affinity ligand introduction amount (protein A immobilization amount)" described above. The protein A immobilization amount thus obtained is shown in the column "Affinity ligand introduction amount" of Table 1.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Comparative Example 1

1. Preparation of Affinity Chromatography Carrier

A protein A-immobilized carboxylated carrier was prepared in the same manner as in Example 1, except that the amount of sodium chloroacetate used was changed from 6.2 g to 1.8 g at the time of preparing the carboxylated carrier (introduction of a carboxy group).

Further, the hydrophilic polymer coating amount, the carboxy group introduction amount, and the affinity ligand introduction amount were measured in the same manner as in Example 1. The measurement results are shown in the columns "Hydrophilic polymer coating amount", "Carboxy group introduction amount", and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Comparative Example 2

1. Preparation of Affinity Chromatography Carrier

A protein A-immobilized carboxylated carrier was prepared in the same manner as in Example 1, except that the amount of sodium chloroacetate used was changed from 6.2 g to 22.7 g at the time of preparing the carboxylated carrier (introduction of a carboxy group).

Further, the hydrophilic polymer coating amount, the carboxy group introduction amount, and the affinity ligand introduction amount were measured in the same manner as in Example 1. The measurement results are shown in the columns "Hydrophilic polymer coating amount", "Carboxy group introduction amount", and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Comparative Example 3

1. Preparation of Affinity Chromatography Carrier (1) Preparation of Carrier—Coating with Hydrophilic Polymer A wet gel of the carrier was obtained in the same manner as in Example 1. Further, the dextran coating amount of the obtained carrier was measured in the same manner as in Example 1, in accordance with the section "Method for measuring hydrophilic polymer coating amount" described above. The obtained hydrophilic polymer coating amount is shown in the column "Hydrophilic polymer coating amount" of Table 1.

(2) Preparation of Protein A-Immobilized Carrier—Introduction of Affinity Ligand The obtained carrier was placed in a disposable column in an amount of 4 mL as a wet volume and washed by repeating suspension and filtration using pure water to obtain a carrier slurry. The pure water was removed from the carrier slurry by suction filtration to obtain a wet gel.

The obtained wet gel was placed in a reaction vessel, and the volume of the slurry was adjusted to 5 mL with pure water. Then, 1 mL of 250 mM sodium citrate buffer (pH 3.5) was added thereto. Further, 2 mL of a 160 mM aqueous sodium periodate solution was added, followed by stirring with inversion of the reaction vessel at room temperature for 0.5 hours, washing by repeated suspension and filtration using pure water and phosphate buffer on the filter, and removing the pure water or phosphate buffer by suction filtration to obtain a wet gel of an aldehyde group-introduced carrier.

1.5 g of the wet gel of the obtained aldehyde group-introduced carrier was placed in a reaction vessel, and 3 mL of a 20 mg/mL protein A solution was added to the reaction vessel, followed by stirring with inversion of the reaction vessel at room temperature for 2 hours. The 20 mg/mL protein A solution was prepared by dissolving recombinant native protein A "rSPA" (manufactured by Repligen Corporation) in 200 mM 2-(N-morpholino)ethanesulfonic acid (MES) buffer (pH 7.4).

Subsequently, 11 mg of triethylaminoborane was added to the reaction vessel which was then shaken at 25° C. for 16 hours. The solvent was replaced with 200 mM MES buffer (pH 7.4), followed by washing. After the washing solution was removed, 3 mL of 20 mM Tris-HCl buffer and 11 mg of triethylaminoborane were added to the reaction vessel, followed by stirring with inversion of the reaction vessel at room temperature for 2 hours. The solvent was replaced with pure water and a 1 M aqueous sodium chloride solution, followed by washing to obtain a protein A-immobilized carrier.

In addition, the protein A immobilization amount (affinity ligand introduction amount) of the protein A-immobilized carrier thus obtained was measured in accordance with the section "Method for measuring affinity ligand introduction amount (protein A immobilization amount)" described above. The protein A immobilization amount thus obtained is shown in the column "Affinity ligand introduction amount" of Table 1.

2. Evaluation of Antibody Adsorption Capacity and Purification Purity

Using the protein A-immobilized carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Comparative Example 4

1. Preparation of Affinity Chromatography Carrier

The crosslinked agarose-based substrate, Sepharose 6 Fast Flow (manufactured by GE Healthcare GmbH) was washed on a glass filter by repeating suspension and filtration using pure water, thereby obtaining a substrate slurry. The pure water was removed from the substrate slurry by suction filtration to obtain a wet gel.

12 g of the obtained wet gel, 4.7 g of sodium chloroacetate and 24 mL of pure water were placed in a 100 mL three-neck flask and stirring of the contents of the flask was started in a warm bath at 50° C. Stirring was carried out until the sodium chloroacetate was completely dissolved. After dissolution, 8.8 g of a 50% (w/w) aqueous sodium hydroxide solution was added dropwise over 1 hour in a warm bath at 50° C. while maintaining the temperature in the flask at about 50° C. After the whole amount of the aqueous sodium hydroxide solution was added dropwise, the mixture was further reacted for 3 hours and washed on a glass filter by repeating suspension and filtration using pure water to obtain a wet gel of the carboxylated carrier.

Using the obtained carboxylated carrier, a protein A-immobilized carboxylated carrier was obtained in the same manner as in Example 1.

Further, the carboxy group introduction amount of the carboxylated carrier and the protein A introduction amount of the protein A-immobilized carboxylated carrier were measured in the same manner as in Example 1. The measurement results are shown in the columns "Carboxy group introduction amount" and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Comparative Example 5

1. Preparation of Affinity Chromatography Carrier

A protein A-immobilized carboxylated carrier was prepared in the same manner as in Comparative Example 4, except that the crosslinked agarose-based substrate was changed to "Sepharose 4 Fast Flow" (manufactured by GE Healthcare GmbH) at the time of preparing the wet gel, and the amount of sodium chloroacetate used was changed from 4.7 g to 9.3 g at the time of preparing the carboxylated carrier.

Further, the carboxy group introduction amount of the carboxylated carrier and the protein A introduction amount of the protein A-immobilized carboxylated carrier were measured in the same manner as in Example 1. The measurement results are shown in the columns "Carboxy group introduction amount" and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Comparative Example 6

1. Preparation of Affinity Chromatography Carrier

As an affinity chromatography carrier, a protein A-introduced carrier "MabSelect SuRe" (manufactured by GE Healthcare GmbH) ("MABSELECT" is a registered trademark) was prepared.

2. Evaluation of Antibody Adsorption Capacity and Purification Purity

Using the protein A-introduced carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Comparative Example 7

1. Preparation of Affinity Chromatography Carrier

A methacrylate-based porous substrate, "TOYOPEARL HW-65F (manufactured by Tosoh Corporation) ("TOYOPEARL" is a registered trademark) was washed on a glass filter by repeating suspension and filtration using pure water, thereby obtaining a substrate slurry. The pure water was removed from the substrate slurry by suction filtration to obtain a wet gel.

12 g of the obtained wet gel, 3.8 g of sodium chloroacetate and 24 mL of pure water were placed in a 100 mL three-neck flask and stirring of the contents of the flask was started in a warm bath at 50° C. Stirring was carried out until the sodium chloroacetate was completely dissolved. After dissolution, 8.8 g of a 50% (w/w) aqueous sodium hydroxide solution was added dropwise over 1 hour in a warm bath at 50° C. while maintaining the temperature in the flask at about 50° C. After the whole amount of the aqueous sodium hydroxide solution was added dropwise, the mixture was further reacted for 3 hours and washed on a glass filter by repeating suspension and filtration using pure water to obtain a wet gel of the carboxylated carrier.

Using the obtained carboxylated carrier, a protein A-immobilized carboxylated carrier was obtained in the same manner as in Example 1.

Further, the carboxy group introduction amount of the carboxylated carrier and the protein A introduction amount of the protein A-immobilized carboxylated carrier were measured in the same manner as in Example 1. The measurement results are shown in the columns "Carboxy group introduction amount" and "Affinity ligand introduction amount" of Table 1, respectively.

2. Evaluation of Antibody Adsorption Capacity and Purification Purity

Using the protein A-immobilized carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Comparative Example 8

1. Preparation of Affinity Chromatography Carrier

A wet gel of the carboxylated carrier was obtained in the same manner as in Example 1.

The obtained wet gel was used as an affinity chromatography carrier.

Further, the hydrophilic polymer coating amount and the carboxy group introduction amount were measured in the same manner as in Example 1. The measurement results are shown in the columns "Hydrophilic polymer coating amount" and "Carboxy group introduction amount" of Table 1, respectively.

2. Evaluation of Antibody Adsorption Capacity and Purification Purity

Using the carboxylated carrier thus prepared, the antibody adsorption capacity and purification purity were evaluated in the same manner as in Example 1, in accordance with the sections "Evaluation method of antibody adsorption capacity" and "Evaluation method of purification purity" described above. The evaluation results of the antibody adsorption capacity and purification purity are shown in the columns "Antibody adsorption capacity (evaluation)" and "Purification purity (evaluation)" of Table 1, respectively.

Reference Example 1

1. Preparation of Chromatography Carrier

As a chromatography carrier, a sulfoxy group-introduced carrier "CELLUFINE MAX S-r" (manufactured by JNC Corporation) ("CELLUFINE" is a registered trademark) was prepared.

2. Evaluation of Antibody Adsorption Capacity and Purification Purity

Using the sulfoxy group-introduced carrier thus prepared, the antibody adsorption capacity and purification purity were evaluated in accordance with the sections "Evaluation method of antibody adsorption capacity" and "Evaluation method of purification purity" to be described later. The evaluation results of the antibody adsorption capacity and purification purity are shown in the columns "Antibody adsorption capacity (evaluation)" and "Purification purity (evaluation)" of Table 1, respectively.

3. Measurement of Sulfoxy Group Introduction Amount

In addition, the sulfoxy group introduction amount was measured in accordance with the section "Method for measuring carboxy group introduction amount" described above, and the sulfoxy group introduction amount thus measured was 150 mmol/L-gel.

4. Evaluation Method of Antibody Adsorption Capacity 1 mL of a commercially available chromatography carrier was packed in a glass column "TRICORN 10/20 column" (manufactured by GE Healthcare GmbH) ("TRICORN" is a registered trademark) which was then connected to a chromatographic system "AKTA avant 25" (manufactured by GE Healthcare GmbH) ("AKTAavant" is a registered trademark), followed by the measurement of antibody adsorption capacity.

After the column was equilibrated with an equilibration solution (10 mM acetate buffer, pH 4.7), 30 mL of a solution prepared by adjusting a human IgG antibody (Immunoglobulin G) to 5 mg/mL with standard buffer (10 mM acetate buffer, pH 4.7) was added thereto at a flow rate of 0.42 mL/min. After washing the column with 5 mL of a post-loading washing solution (10 mM acetate buffer, pH 4.7) at the same flow rate, 30 mL was allowed to flow at the same flow rate while gradually increasing the salt concentration with an eluant 1 (20 mM phosphate buffer, pH 7.4) and an eluant 2 (20 mM phosphate buffer, 1 M NaCl, pH 7.4). Thereafter, 5 mL of a CIP solution (0.1 M aqueous sodium hydroxide solution) was allowed to flow at the same flow rate and then 5 mL of an equilibration solution (20 mM phosphate buffer, 150 mM NaCl, pH 7.4) was allowed to flow at the same flow rate. At this time, the antibody elution amount of the eluate in each fraction was calculated from the IgG elution peak obtained by monitoring the absorbance at 280 nm. The amount of antibodies eluted from the pre-elution washing solution to the CIP solution was calculated as the antibody adsorption capacity.

The antibody adsorption capacity was evaluated based on the antibody adsorption capacity in the case where only a carboxy group and protein A were introduced, according to the following evaluation standards. That is, the antibody adsorption capacity was evaluated based on Comparative Example 4.

Antibody adsorption capacity is 40% or more of the standard Evaluation of antibody adsorption capacity "A"

Antibody adsorption capacity is less than 40% of the standard Evaluation of antibody adsorption capacity "C"

5. Evaluation Method of Purification Purity 1 mL of a commercially available chromatography carrier was packed in a glass column "TRICORN 10/20 column" (manufactured by GE Healthcare GmbH) ("TRICORN" is a registered trademark) which was then connected to a chromatographic system "AKTA avant 25" (manufactured by GE Healthcare GmbH) ("AKTAavant" is a registered trademark), followed by the measurement of the amount of host cell protein (HCP) and the amount of Immunoglobulin G (IgG) eluted from each fraction.

After the column was equilibrated with an equilibration solution (10 mM acetate buffer, pH 4.7), an IgG/HCP mixed solution prepared by using standard buffer (10 mM acetate buffer, pH 4.7), so that IgG and HCP derived from a Chinese Hamster Ovary S (CHO-S) cell were 1.6 mg/mL and 0.64 mg/mL, respectively, was added at a flow rate of 0.21 mL/min such that an antibody amount of 80% of the antibody adsorption capacity obtained in the above (1) was loaded. Thereafter, 30 mL was allowed to flow at a flow rate of 0.42 mL/min while gradually increasing the salt concentration with an eluant 1 (20 mM phosphate buffer, pH 7.4) and an eluant 2 (20 mM phosphate buffer, 1 M NaCl, pH 7.4). Thereafter, 5 mL of a CIP solution (0.1 M aqueous sodium hydroxide solution) was allowed to flow at the same flow rate and then 5 mL of an equilibration solution (20 mM phosphate buffer, 150 mM NaCl, pH 7.4) was allowed to flow at the same flow rate. At this time, the IgG elution amount of the eluate in each fraction was calculated from the IgG elution peak obtained by monitoring the absorbance at 280 nm. The eluate of each fraction was recovered and the amount of HCP of the eluate in each fraction was calculated by ELISA using a host cell protein detection kit "CHO HCP 3rd Generation ELISA kit" (manufactured by Cygnus Technologies, Inc.).

Using the calculated IgG amount and HCP amount of the eluate, the purification purity was calculated according to the following equation in terms of HCP incorporation amount in the eluate, that is, HCP amount per IgG amount in the eluate.

Purification purity (ppm)=HCP incorporation amount (ppm)=HCP amount of eluate/IgG amount of eluate The purification purity was evaluated based on the incorporated amount of HCP (ppm) in the case where only a carboxy group and protein A were introduced, according to the following evaluation standards. That is, the HCP incorporation amount was evaluated based on Comparative Example 4.

HCP incorporation amount (ppm) decreased by 20% or more Evaluation of purification purity "A"

HCP incorporation amount (ppm) decreased by more than 0% and less than 20% Evaluation of purification purity "B"

HCP incorporation amount (ppm) did not decrease Evaluation of purification purity "C"

TABLE 1

| | | Substrate | Hydrophilic polymer Upper: type Lower: intrinsic viscosity [dL/g] | Hydrophilic polymer coating amount [mg/g-dry gel] | Carboxy group introduction amount [mmol/L-gel] | Affinity ligand | Affinity ligand introduction amount [mmol/L-gel] | Antibody adsorption capacity (evaluation) | Purification purity (evaluation) |
|---|---|---|---|---|---|---|---|---|---|
| Examples | 1 | Sepharose 6 FF (crosslinked agarose-based) | Dextran 70 0.23 | 22 | 27 | Protein A | 0.16 | A | A |
| | 2 | Sepharose 6 FF (crosslinked agarose-based) | Dextran 70 0.23 | 22 | 19 | Protein A | 0.19 | A | A |
| | 3 | Sepharose 6 FF (crosslinked agarose-based) | Dextran 70 0.23 | 22 | 54 | Protein A | 0.17 | A | B |
| | 4 | Sepharose 6 FF (crosslinked agarose-based) | Dextran 70 0.23 | 209 | 27 | Protein A | 0.14 | A | A |
| | 5 | Sepharose 4 FF (crosslinked agarose-based) | Dextran 70 0.23 | 215 | 33 | Protein A | 0.16 | A | A |
| | 6 | Sepharose 4 FF (crosslinked agarose-based) | Dextran 40 0.17 | 156 | 32 | Protein A | 0.19 | A | A |
| | 7 | Sepharose 4 FF (crosslinked agarose-based) | Dextran 19 0.12 | 96 | 29 | Protein A | 0.20 | A | B |
| | 8 | TOYOPEARL HW-65F (methacrylate-based) | Dextran 40 0.17 | 37 | 29 | Protein A | 0.13 | A | B |
| Comparative Examples | 1 | Sepharose 6 FF (crosslinked agarose-based) | Dextran 70 0.23 | 22 | 11 | Protein A | 0.10 | C | A |
| | 2 | Sepharose 6 FF (crosslinked agarose-based) | Dextran 70 0.23 | 22 | 84 | Protein A | 0.18 | A | C |
| | 3 | Sepharose 6 FF (crosslinked agarose-based) | Dextran 70 0.23 | 22 | — | Protein A | 0.13 | A | C |

TABLE 1-continued

| | | Substrate | Hydrophilic polymer Upper: type Lower: intrinsic viscosity [dL/g] | Hydrophilic polymer coating amount [mg/g-dry gel] | Carboxy group introduction amount [mmol/L-gel] | Affinity ligand | Affinity ligand introduction amount [mmol/L-gel] | Antibody adsorption capacity (evaluation) | Purification purity (evaluation) |
|---|---|---|---|---|---|---|---|---|---|
| | 4 | Sepharose 6 FF (crosslinked agarose-based) | — — | — | 18 | Protein A | 0.17 | A | C |
| | 5 | Sepharose 4 FF (crosslinked agarose-based) | — — | — | 26 | Protein A | 0.17 | A | C |
| | 6 | MabSelect SuRe (crosslinked agarose-based) | — — | — | — | Protein A (alkali-resistant) | Not shown | A | C |
| | 7 | TOYOPEARL HW-65F (methacrylate-based) | — — | — | 35 | Protein A | 0.10 | A | C |
| | 8 | Sepharose 6 FF (crosslinked agarose-based) | Dextran 70 0.23 | 22 | 27 | — | — | C | C |
| Reference Example | 1 | CELLUFINE MAX S-r (crosslinked cellulose-based) | Dextran Not shown | Not shown | (150) (sulfoxy group) | — | — | A | C |

EXPLANATION OF RESULTS

Each of the affinity chromatography carriers of Examples 1 to 8 was evaluated as having antibody adsorption capacity and purification purity of "B" or higher, and exhibited excellent antibody adsorption capacity and excellent purification purity.

On the other hand, in Comparative Examples 1 to 8, at least one of the antibody adsorption capacity or purification purity was evaluated as "C", and at least one of the antibody adsorption capacity or purification purity was inferior.

In addition, in the case of comparing Example 6 with Example 8, the purification purity in Example 6 in which the substrate is crosslinked agarose-based was evaluated as "A", whereas the purification purity in Examples 8 in which the substrate was methacrylate-based was evaluated as "B", and it was therefore suggested that the purification purity in the case of the crosslinked agarose-based substrate was superior to that in the case of the methacrylate-based substrate. In Examples 1 and 4 in which the hydrophilic polymer coating amounts were greatly different from each other, the purification purity in both cases was evaluated as "A". Therefore, it is considered that the reason why the evaluation of the purification purity differs between Example 6 and Example 8 is due to whether the substrate is crosslinked agarose-based (Example 6) or methacrylate-based (Example 8).

What is claimed is:

1. An affinity chromatography carrier, comprising:
a substrate;
a hydrophilic polymer; and
an affinity ligand, wherein
the substrate is comprised of at least one selected from the group consisting of agarose and crosslinked agarose,
the hydrophilic polymer is at least one selected from the group consisting of hydrophilic polysaccharides,
the substrate is coated with the hydrophilic polymer,
the affinity ligand is at least one selected from the group consisting of an antibody-binding protein and an antibody-binding polypeptide,
a carboxy group is introduced into the affinity chromatography carrier,
the amount of the carboxy group introduced is 15 mmol/L-gel to 60 mmol/L-gel in terms of ion exchange capacity, and
the coating amount of the hydrophilic polymer is from 3 to 240 mg/g-dry gel.

2. The affinity chromatography carrier according to claim 1, wherein the hydrophilic polymer has an intrinsic viscosity of 0.10 dL/g or more.

3. The affinity chromatography carrier according to claim 2, wherein the hydrophilic polymer is at least one selected from the group consisting of dextran, carboxymethyl dextran and pullulan.

4. The affinity chromatography carrier according to claim 1, wherein the hydrophilic polymer is at least one selected from the group consisting of dextran, carboxymethyl dextran and pullulan.

5. The affinity chromatography carrier according to claim 1, wherein the substrate is a porous particle.

6. The affinity chromatography carrier according to claim 1, wherein the affinity ligand undergoes an antigen-antibody reaction with an antibody.

7. The affinity chromatography carrier according to claim 1, wherein the affinity ligand is protein A or a variant thereof.

8. The affinity chromatography carrier according to claim 1, wherein the substrate is comprised of at least one selected from the group consisting of agarose and crosslinked agarose,
the hydrophilic polymer is at least one hydrophilic polysaccharide selected from the group consisting of dextran, carboxymethyl dextran and pullulan,
the intrinsic viscosity of the hydrophilic polysaccharide is 0.12 dL/g to 0.30 dL/g,
the coating amount of the hydrophilic polymer is 10 mg/g-dry gel to 240 mg/g-dry gel,
the amount of the carboxy group introduced is 15 mmol/L-gel to 55 mmol/L-gel in terms of ion exchange capacity,
the affinity ligand is protein A or a variant thereof, and the amount of the affinity ligand introduced is 0.10 mmol/L-gel to 1.0 mmol/L-gel.

9. A purification method for purifying a biological substance by adsorbing and eluting. the biological substance as the biological substance passes through a column packed with the affinity chromatography carrier according to claim 1.

10. The purification method according to claim 9, wherein the pH in the adsorbing of the biological substance is 5.0 to 9.0.

11. The purification method according to claim 9, wherein the pH in the eluting of the biological substance is 2.0 to 5.0.

12. The purification method according to claim 9, wherein the biological substance is an antibody or an antibody derivative.

\* \* \* \* \*